(12) United States Patent
Smith et al.

(10) Patent No.: US 11,501,879 B2
(45) Date of Patent: Nov. 15, 2022

(54) VOICE CONTROL FOR REMOTE MONITORING

(71) Applicant: Preventice Technologies, Inc, Rochester, MN (US)

(72) Inventors: Richard M. Smith, Oronoco, MN (US); Scott J. Burrichter, Rochester, MN (US); Jon P. Otterstatter, Saint Paul, MN (US)

(73) Assignee: PREVENTICE TECHNOLOGIES, INC., Rochester, MN (US)

( * ) Notice: Subject to any disclaimer, the term of this patent is extended or adjusted under 35 U.S.C. 154(b) by 177 days.

(21) Appl. No.: 16/589,351

(22) Filed: Oct. 1, 2019

(65) Prior Publication Data

US 2020/0160991 A1    May 21, 2020

Related U.S. Application Data

(60) Provisional application No. 62/739,700, filed on Oct. 1, 2018.

(51) Int. Cl.
*G16H 40/67* (2018.01)
*G10L 15/26* (2006.01)
*G06F 40/205* (2020.01)
*G06F 3/16* (2006.01)

(52) U.S. Cl.
CPC ............ *G16H 40/67* (2018.01); *G06F 3/167* (2013.01); *G06F 40/205* (2020.01); *G10L 15/26* (2013.01)

(58) Field of Classification Search
CPC ........ G16H 40/67; G16H 70/20; G10L 15/26; G06F 40/205; G06F 3/167; G06F 40/284

USPC .......................................................... 600/300
See application file for complete search history.

(56) References Cited

U.S. PATENT DOCUMENTS

| | | | |
|---|---|---|---|
| 6,856,960 B1 * | 2/2005 | Dragosh ............. | H04M 3/4936 704/E15.047 |
| 7,930,191 B1 * | 4/2011 | Rogers .................... | G16H 10/60 705/2 |
| 9,424,845 B2 * | 8/2016 | Weng ...................... | G10L 17/22 |
| 9,653,082 B1 * | 5/2017 | Jochumson ............. | G10L 15/22 |
| 9,740,751 B1 * | 8/2017 | Yeom ...................... | G06F 3/167 |
| 10,229,755 B1 * | 3/2019 | Anumalasetty ........ | G16H 10/20 |
| 2005/0021342 A1 * | 1/2005 | Major ..................... | G10L 15/26 704/E15.044 |
| 2007/0168225 A1 * | 7/2007 | Haider ................... | G16H 10/20 705/2 |
| 2009/0043580 A1 * | 2/2009 | Mozer .................... | G10L 15/26 704/251 |

(Continued)

*Primary Examiner* — Stephen S Hong
*Assistant Examiner* — Broderick C Anderson
(74) *Attorney, Agent, or Firm* — Faegre Drinker Biddle & Reath LLP (57) ABSTRACT

Techniques for voice control of a patient care device are described. A patient care device receives an audio request from a user. The patient care device records the audio request. The patient care device transmits the audio request over a communication network to a speech recognition service, and in response receives, from the speech recognition service, a textual representation of the audio request. The patient care device matches the textual representation, using the computer processor, to a first command in a vocabulary of available commands, and in response performs the first command.

16 Claims, 5 Drawing Sheets

(56) References Cited

U.S. PATENT DOCUMENTS

| | | | | |
|---|---|---|---|---|
| 2012/0166203 A1* | 6/2012 | Fuchs | ................ | G16H 40/20 |
| | | | | 704/275 |
| 2014/0006943 A1* | 1/2014 | Robbins | ............ | H04L 67/025 |
| | | | | 715/273 |
| 2015/0040244 A1* | 2/2015 | DeBenedictis | ... | H04L 63/102 |
| | | | | 709/204 |

* cited by examiner

Figure 5

VOICE CONTROL FOR REMOTE MONITORING

BACKGROUND

Portable monitoring devices for collecting biometric data are becoming increasingly common in diagnosing and treating medical conditions in patients. Patients can interact with the remote monitoring devices using text-based or graphical user interfaces. It can be difficult, however, for patients to navigate and use the interfaces or even to find what they are looking for in the interface. A patient that has trouble navigating the interface may use the monitoring devices incorrectly or may stop using the monitoring devices entirely. This can be detrimental to the patient's health, and harmful to the user experience.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate typical embodiments and are therefore not to be considered limiting; other equally effective embodiments are contemplated.

DESCRIPTION OF EXAMPLE EMBODIMENTS

Overview

An embodiment described herein is a computer-implemented method for voice control of a patient care device. The method includes receiving an audio request from the user. The method further includes recording the audio request and transmitting the audio request over a communication network to a speech recognition service. The method further includes receiving, from the speech recognition service, a textual representation of the audio request. The method further includes matching the textual representation to a command in a vocabulary of available commands. The method further includes carrying out the matched command.

A further embodiment described herein is a computer-implemented method for providing audio guidance to a patient from a patient care device. The method includes receiving an unprompted command from the user at the patient care device. The method further includes analyzing an audio configuration parameter and determining that audio guidance is allowed. The method further includes, in response to determining that audio guidance is allowed, providing audio guidance to the user from the patient care device.

Example Embodiments

According to one or more techniques disclosed herein, voice (or audio) commands can be used to control a patient care device, for example a mobile device used with a biometric monitoring sensor. In an embodiment, voice commands can be used for all aspects of a patient care device. For example, a patient care device may be controlled using a patient care application on a patient's computer or smartphone. This application can be operated using a graphical user interface. In addition (or instead) of the graphical user interface, according to one or more techniques disclosed herein the application can be controlled using voice commands. This can improve the usability of the application by supplementing relatively small buttons, and a potentially complex user interface, with a voice control interface.

With a voice control interface, the user can use natural language to control the application and navigate (via command) to anywhere in the application without following menus. For example, the user can request guidance about a feature of the application (e.g., "What does this light mean?") or can control the application using a voice command (e.g., by responding to a symptom prompt).

In an embodiment, the voice control is two-way, meaning that the device on which the application is running (e.g., a smartphone, tablet, or computer) can provide audio guidance to the user, and the user can provide voice (or audio) commands to the application.

In an embodiment, the voice command from the user can be parsed using a speech recognition service provided using a third party Software Development Kit (SDK). For example, in an embodiment and as discussed in more detail below, the patient care application can record the voice command from the user, transmit the recorded audio to a natural language recognition service, and receive in response a textual representation of the content of the audio command. Alternatively, the patient care application can include a speech recognition service to parse the voice command.

In an embodiment, the speech recognition service (whether implemented as a remote service or as part of the patient care application) can include a training module to improve its understanding of a user's voice commands. In one embodiment, the training module initiates a training phase when a user begins using voice commands. This training phase can, for example, request that the user engage in training to allow the speech recognition service to better understand the user's voice (e.g., by requesting that the user pronounce particular words or phrases). Alternatively, or in addition, the training module can continually train the speech recognition service to better understand the user's voice. For example, the speech recognition service can compare received vocal commands with the identified corresponding function, and use this information to continually improve the speech recognition service. In an embodiment, the speech recognition service can recognize different users of the patient care application and can train to better understand each user's voice as he or she provides a voice command.

In an embodiment, the patient care application has access to a care protocol for the patient (as discussed below in relation to FIGS. 1-5) and uses this care protocol to identify and carry out the command based on the parsed text. For example, a care protocol can specify particular symptom prompts, reminders, treatment thresholds, etc.

Further, in an embodiment, the patient care application with voice control is integrated with a patient care platform, allowing for further voice controls. For example, if the care protocol is changed (for example, ended early), the application could use audio guidance to explain how to return the monitoring equipment. Further, ad hoc messaging from the patient's care team could be provided through the application using audio guidance.

In an embodiment, the patient care application includes controls to allow the user to configure the voice commands and guidance to remain discrete. For example, in an embodiment, the patient care application can be configured to control which (if any) messages or alerts will be spoke, and under what conditions. Further, the patient care application can be configured to control which (if any) spoken requests from the user are treated as voice commands.

In an embodiment, voice commands can be used for numerous features related to the biometric monitoring device and the patient care application. For example, voice commands could be used for: initial set-up of the device (e.g., explaining to the user how to put the monitoring device on, use the monitoring system, etc.), reminding the user to perform tasks (e.g. take your blood pressure or check your weight), alerting the user to actions that are needed (e.g. electrodes are detached), and prompting the user for symptoms (e.g., when the user presses the symptom button on the device, the patient care application could ask the user for their symptoms and the user could answer the query using their voice).

As another example, voice commands could be used to allow the user to query the system status. For example, the user could use voice commands to: ask whether the device is currently monitoring, confirm that the device is operating properly, check when data was last received from the monitoring device, check when data was last sent to the server, check how much data is pending to send to the server, check the battery levels, check how long the device has been monitoring, check when monitoring will be complete, etc. As another example, voice commands and guidance could be used to control the patient care application. For example, the user could use voice commands to receive guidance about switching devices, pause monitoring, and resume monitoring. As another example, voice commands and guidance could be used to provide the user with additional help or information about the patient care application and biometric monitoring devices. For example, the user could use voice commands to ask what a particular light or symbol means, ask what the user should do while showering or another daily activity, ask where and how the user should wear the device, etc.

Patient Care Environment

Figure 1:
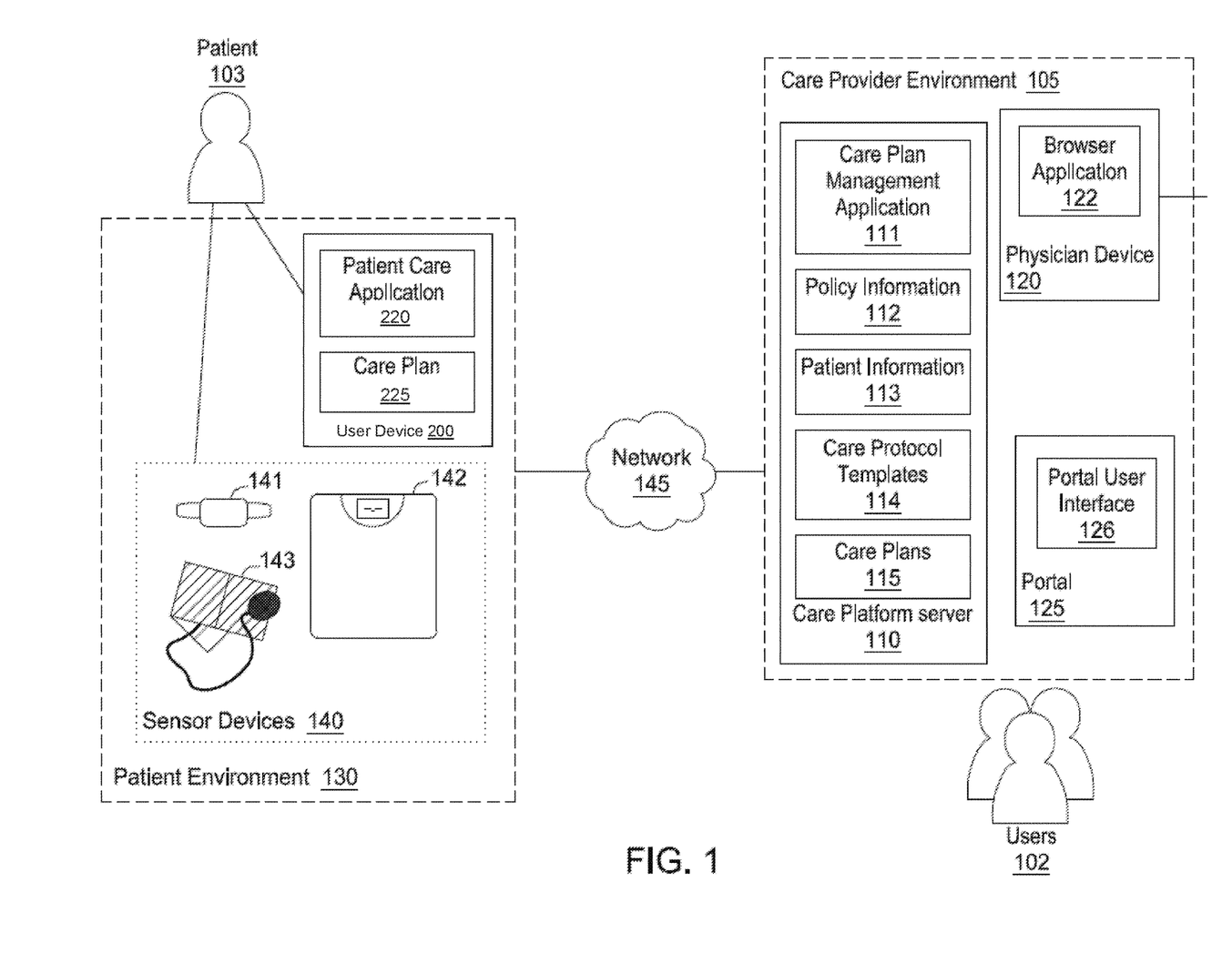
FIG. 1 illustrates an example computing environment, according to one embodiment.

FIG. 1 illustrates an example computing environment 100, according to one embodiment. As shown, the computing environment 100 may include a care provider environment 105 and a patient environment 130, each connected to one another via a network 145. The environments 105 and 130 allow a patient 103 to communicate with a care provider 101 (e.g., a physician).

The care provider environment 105 includes a care platform server 110, a physician device 120, and a portal 125. Each of the care platform server 110, physician device 120, and portal 125 may be a physical computing system or may be a virtual computer instance (e.g., executing in a cloud computing platform). A care provider 101 may use the physician device 120 to access (e.g., via a browser application 122) a portal user interface 126 hosted by the portal 125. The portal user interface 126 itself provides users 102 (e.g., the care providers 101, the patient, authorized members of the patient's family, etc.) with access to the care platform server 110.

The care platform server 110 includes various applications and data that allow a care provider 101 to create and manage a care plan for a patient 103. As shown, the care platform server 110 includes a care plan management application 111, policy information 112, patient information 113, care protocol templates 114, and care plans 115. The care plan management application 111 generates care plans 115 based on care protocol templates 114.

A care plan 115 may be created based on one or more care protocols, with each of the care protocols relating to a respective medical condition the patient has been diagnosed with. A care protocol is a set of tasks that a patient 103 follows to manage a certain condition, metrics that the care plan management application 111 monitors, objectives for the patient to meet, and the like. For instance, a care protocol may target recovery from a heart attack. Another care protocol may treat diabetes. Tasks associated with a care protocol may include steps such as exercising for a specified duration or taking medication at a certain time of day.

Further, each care plan protocol may be divided into different phases. The phases may represent different stages of care for a particular condition, e.g., a recovery phase, a maintenance phase, etc., where each phase may include a respective set of tasks for the patient to perform, observation metrics to monitor, observation thresholds to detect when the monitored metrics satisfy specified conditions. For example, a care protocol for weight management may include several phases. A patient 103 may begin the care protocol at a weight loss phase, where tasks may include performing strenuous exercises frequently, and where thresholds may specify further actions that the care plan management application 111 takes if the patient 103 loses X amount of weight or gains Y amount of weight. For example, if the metrics indicate that the patient 103 gained Y amount of weight after a period at which the patient 103 had a Z average activity level, the care plan management application 111 may instruct the patient 103 to watch an educational video in response. Continuing the example, if the patient 103 loses X amount of weight during a given period, the care plan management application 111 may transition the care protocol to a weight maintenance phase, where tasks may include exercises that assist the patient 103 in maintaining the weight.

Each care plan protocol may also include observation thresholds associated with monitored metrics and could further specify an action(s) to be taken responsive to an observation threshold being satisfied. The care platform server 110 may monitor the adherence of a patient 103 through various sensor devices 140 that can measure heart rate, weight, blood pressure, and the like. The care platform server 110 may take specified actions if one of the metrics crosses a corresponding threshold, e.g., if a patient 103 gains 1.5 pounds after a day, the platform server 110 may report the weight gain to the care provider 101.

To generate a care plan, a care provider 101 may configure care protocol templates 114 corresponding to medical conditions the patient 103 is diagnosed with. To do so, the care provider 101 (e.g., via the portal user interface 126) selects one or more care protocol templates 114 to associate with the patient 103. The care plan management application 114 populates a care plan with tasks, triggers, and monitoring thresholds as specified by the selected care protocol templates 114. The portal user interface 126 may display the selected care protocol templates 114, where the care provider 101 may customize various facets of each selected template 114, such as tasks and thresholds. For example, the care provider 101 may customize a task instructing a patient to check blood pressure every morning. The care provider 101 may adjust the task so that the patient checks blood pressure twice a day. In addition, the care provider 101 may adjust thresholds associated with that task, such that the care platform server 110 alerts the care provider 101 if a threshold blood pressure is reached.

In one embodiment, each customization may be subject to comply with policy information 112 and such compliance may be enforced by the care plan management application 111 during the creation of the care plan. Policy information 112 may include various guidelines (e.g., set by a hospital, standards organization, insurance companies, etc.) that each care protocol must adhere to. For instance, the policy information 112 may specify milligram ranges for certain medications that may be assigned to a patient 103 in a care protocol. The care plan management application 111 may enforce such policy information 113 to ensure a care provider 101 configuring a care plan does not customize tasks beyond the bounds of the policy information 113.

The care plan management application 111 generates a care plan 115 for a patient 103 based on the customizations made by the care provider 101. In doing so, the care plan management application 111 identifies conflicting tasks across the selected care protocol templates 114. For example, a care protocol for high blood pressure may include a task instructing a patient to take 85 milligrams of aspirin three times a day, while another care protocol for a sprained ankle includes a task instructing the patient to take 100 milligrams of aspirin three times a day.

Generally, the patient information 113 represents patient-specific information describing a patient's medical history and treatment history. In one embodiment, the care plan management application 111 may generate the care plan 111 based on the patient information 113, in addition to customizations to care protocol templates 114 that the care provider 101 provides. Patient information 113 may include medications previously prescribed to the patient 103 and whether the medications had a beneficial or adverse effect towards the patient. In a case where a particular medication has had an adverse effect towards a patient 103, the care plan management application 111 may flag tasks associated with taking the medication to the care provider 101 configuring the care plan 115. In response, the care provider 101 may edit or remove the task.

Once generated, the care plan management application 110 may store the care plan 115 on the care platform server 110. Further, the care plan management application 110 transmits the care plan 115 to a user device 200 (e.g., to a patient care application 220 executing on the user device 200) of the patient 103. Information dialogs related to the care plan (shown as care plan 225) can be provided to the patient 103 through input/output devices of the mobile device. For example, the patient care application 220 could generate a graphical user interface including the information dialogs and could present the graphical user interface to the patient via a display device of the user device 200. As another example, the patient care application 220 could output an educational video detailing how to properly perform a particular exercise prescribed for the patient 103 as part of the care plan 225, using the display device and one or more speaker devices of the user device 200. As a further example, as discussed further in relation to FIGS. 3-5, the patient care application 220 could provide an audio, or voice, interface, through which a user could provide voice commands and receive audio guidance.

Moreover, the user device 200, upon receiving the care plan, could configure one or more monitoring devices to monitor one or more patient metrics as specified by the care plan. For example, the user device 200 could configure logic on a heart rate monitor device worn by the patient to monitor the patient's heart rate and to detect when the patient's heart rate exceeds a threshold number of beats per minute specified within the care plan. The heart rate monitor device, upon detecting that the threshold condition has been satisfied, could transmit an alert to the user device 200, which could in turn perform an action as specified by the care plan. For example, the user device 200, upon receiving the alert, could display a notification to the patient, informing the patient that his heart rate is elevated and instructing the patient to sit down and rest for a period of time. As another example, the user device 200 could generate a notification to the care plan management application 111, informing the care plan management application 111 that the patient's heart rate exceeds the threshold amount of beats per minute. Doing so allows for patient events to be detected immediately by the corresponding monitoring device 140, rather than waiting on the care plan management application 111 to parse through the log of data collected from the various sensor devices 140.

The patient care application 220 may display information related to the care plan 225, such as phases, tasks, and other information about conditions targeted for treatment by the care plan 225. When the patient 103 performs a task, the patient 103 records progress in the patient care application 220. The patient care application 220 relays this information to the care plan management application 111. Doing so allows the care provider 101 to monitor the metrics of the patient 103 and adherence to the care plan. Further, depending on how the patient 103 responds to the care plan 225, the care plan management application 111 may adjust certain tasks. For example, the patient 103 could be assigned the task of reading particular educational content every morning as part of the administration of the care plan 225. If the care plan management application 111 then detects that the patient 103 is infrequently completing the assigned task, the care plan management application 111 could alter the care plan 225 to provide the educational content through a different medium. For instance, the care plan management application 111 could alter the care plan 225 such that the patient is assigned to watch an educational video on the same topic as the written educational content, using the user device 200 once per week. Doing so allows the care plan 225 to be adjusted to suit the individual preferences of the patient 103, while helping to ensure that the patient 103 completes the assigned tasks laid out in the care plan 225.

In one embodiment, sensor devices 140 may interact with the patient care application 220 and assist the patient 103 in reporting body-related metrics to the care platform server 110. As shown, such sensor devices 140 may include a body sensor 141, a weighing scale 142, and a blood pressure cuff 143. Each of the sensor devices 140 may capture different metrics of the patient 103. For example, when applied to the body of patient 103, the body sensor 141 captures biometric data (e.g., heart rate, electrocardiogram (ECG) data, etc.) in real-time. In addition, each of the sensor devices 140 may be configured to transmit the metrics electronically to the patient care application 220 on the user device 200. In turn, the patient care application 220 sends the captured metrics to the care plan management application 111.

In one embodiment, the sensor devices 140, upon detecting an observation threshold has been reached, are configured to perform an initial classification of the event. In a particular embodiment, the user device 200 is configured to perform the initial classification of the event. For example, the body sensor 141, upon detecting that the ECG data collected from the patient 103 indicates an erratic heart behavior, could classify the event as a cardiac event. This initial classification, along with the relevant ECG data (e.g., ECG data a predetermined length of time before and after the event), could be transmitted to the user device 200 (e.g., over a Bluetooth® communications link) and the patient care application 220 could then forward the event data on to the care plan management application 111 over the network 145 (e.g., the Internet or any other suitable communication network). Upon receiving the event data, the care plan management application 111 could detect that the event was initially classified as a cardiac event and could perform a more detailed analysis of the event data to more accurately classify the event. For example, the care plan management application 111 could be configured recognize a number of sub-classifications of cardiac events and could analyze the received event to determine which of the sub-classifications best matches the event data. The care plan management application 111 could then record the determined sub-classification. Of note, in some situations, the care plan management application 111 could determine that a particular event is properly classified as multiple sub-classifications. Additionally, in some embodiments, the care plan management application 111 could perform a more in-depth analysis to potentially eliminate certain classifications (e.g., a false positive).

In some situations, the care plan 115 for the patient 103 could specify a particular treatment plan to perform upon determining a particular sub-classification of event. In such a situation, the care plan management application 111 could transmit a request to the patient care application 220 to initiate the treatment plan on the user device 200. Doing so allows for a more computationally expensive analysis of the event data to be performed using the computing resources of the care provider environment 105, rather than the limited resources of the sensor devices 140 or the user device 200, while quickly determining an initial classification for the event using the sensor devices 140.

In one embodiment, the care plan management application 111 is configured to provide feedback to the patient 103 and to adjust the provided feedback over time based on the patient's behavior and preference. For example, an exemplary care plan 115 could prescribe continuing education activities related to the patient's condition and the initial care plan 115 could specify that the patient is to read a weekly article on an aspect of the patient's condition each week. The care plan management application 111 could then monitor the patient's adherence to the assigned task of reading continuing education articles according to the prescribed schedule. For example, if the care plan management application 111 accesses the articles using the mobile device, the care plan management application 111 could record each time the patient accesses the articles and when the patient does not review a particular week's article. As another example, in an embodiment where the patient reviews the articles using a device other than the user device 200, the patient care application 220 could provide an interface through which the patient can provide input specifying that the patient has reviewed the week's article and the care plan management application 111 could detect weeks when no input is received, thus indicating that the patient did not review that week's article. Additionally, in one embodiment, the patient care application 220 is configured to provide an interface to test the patient's knowledge of the content of the week's article. Thus, the patient care application 220 could present an interface including several questions for the patient to answer and the patient care application 220 could determine the patient reviewed that week's article if patient achieved a threshold level of correct answers.

The care plan management application 111 could continue to monitor the patient's adherence to the assigned task and, upon determining that the patient's adherence is sufficiently low (e.g., below a threshold amount of adherence), the care plan management application 111 could alter the patient's care plan in an attempt to boost the patient's adherence to the assigned task. For instance, the care plan management application 111 could alter the schedule at which the prescribed tasks are to be performed, e.g., altering the day of the week on which the task is to be performed, altering the duration of the task, increasing the window of time during which the patient can complete the task and be considered on time, and so on.

In one embodiment, the care plan management application 111 is configured to adjust the assigned task based on the patient's level of adherence to the assigned task. For instance, if the care plan management application 111 detects that the patient is poorly adhering to the assigned task of reading a weekly continuing educational article related to a condition the patient is diagnosed with, the care plan management application 111 could alter the patient's care plan to assign a different task to the patient to attempt to improve the patient's adherence. For example, the care plan management application 111 could remove the task of reading a weekly article from the patient's care plan and could replace the task with a new task of watching a weekly educational video on an aspect of the diagnosed condition, e.g., using the mobile device. The care plan management application 111 could continue monitoring the patient's adherence to the newly assigned task and could make further changes to the patient's care plan in the event the patient's adherence continues to suffer.

In determining how to modify the assigned task, the care plan management application 111 can consider historical patient information for the patient. For example, continuing the above example, the care plan management application 111 could replace the assigned task of reading an educational article with the task of watching a weekly video, and could the care plan management application 111 could then determine that the patient's level of adherence to the assigned task significantly increased. In addition, the care plan management application 111 can consider patient demographic information in selecting an optimal replacement task. For example, based on the patient's age, the care plan management application 111 could determine that the patient is more likely to prefer video content to literary content, and thus the care plan management application 111 could give a preference to video content when inserting tasks into the patient's care plan.

The care plan management application 111 could then save patient data indicating the alteration made to the care plan and that the alteration resulted in a positive effect on the patient's level of adherence. In subsequently modifying other aspects of the patient's care plan, the care plan management application 111 could access this patient data and could determine that the patient appears to adhere more closely to assigned tasks involving video media than tasks involving textual materials. Accordingly, the care plan management application 111 could give a preference to assigned tasks involving video content in modifying the patient's care plan. Doing so provides an individually tailored care plan that is dynamically adjusted based on the patient's individual preferences (and potentially compared to expected responses of similar other users from the patient's demographic as well).

Figure 2:
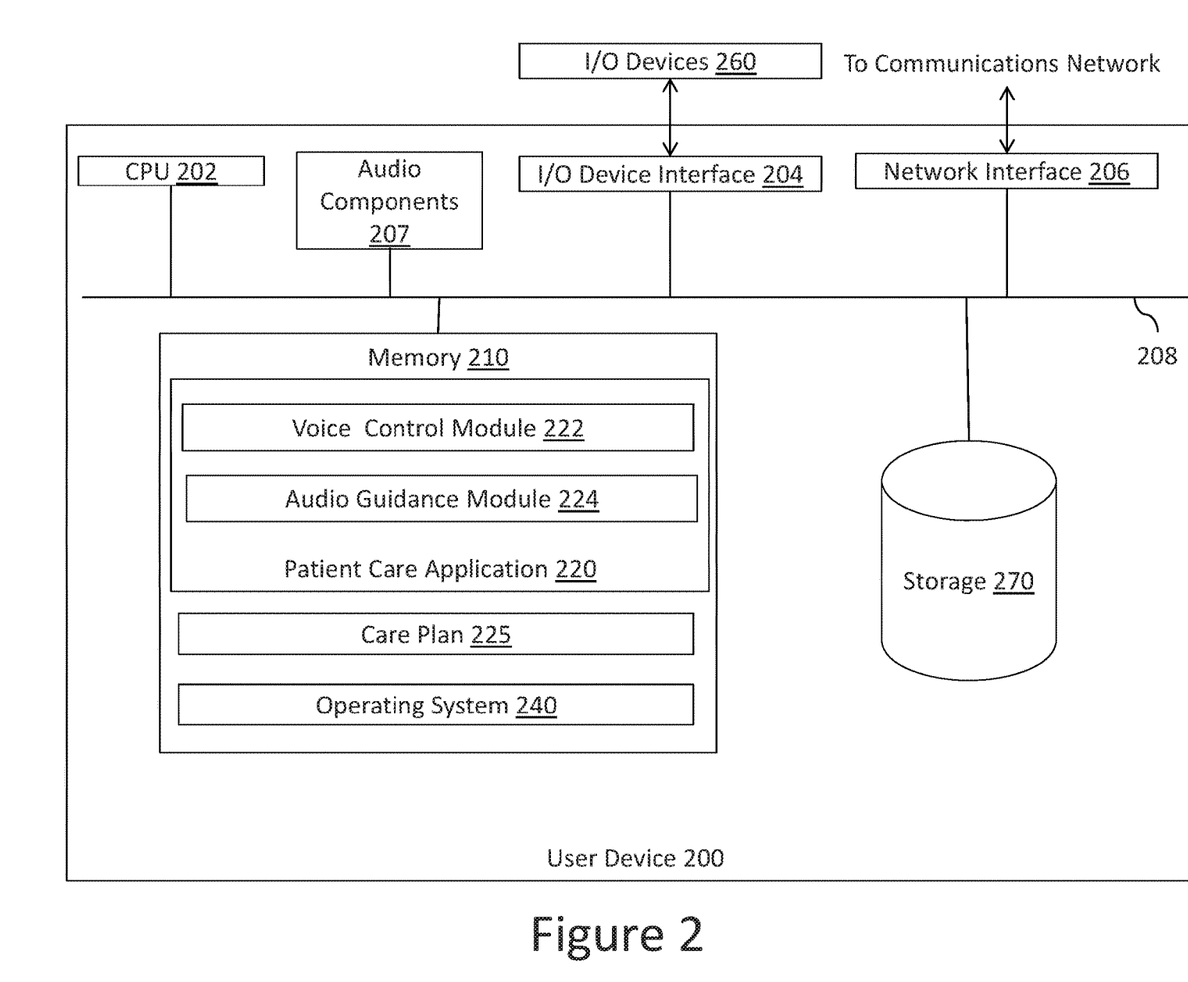
FIG. 2 is a block diagram illustrating a user device, according to one embodiment.

FIG. 2 is a block diagram illustrating a user device 200, according to one embodiment described herein. In an embodiment, the user device 200 is a mobile device (e.g., a smartphone or tablet). Alternatively, the user device 200 is a personal computer or any other suitable user device. As shown, the user device 200 includes, without limitation, a central processing unit (CPU) 202, a network interface 206, audio components (e.g. microphone and speakers) 207, memory 210, and storage 270, each connected to a bus 208. In an embodiment, the user device 200 also includes an Input/Output (I/O) device interface 204 for connecting to I/O devices 260. In an embodiment, the I/O devices 260 can be external I/O devices (e.g., keyboard, display and mouse devices). Alternatively, the I/O devices 260 can be built in I/O devices (e.g., a touch screen display or touchpad). The audio components 207 can be components suitable to facilitate voice control and guidance, including a microphone, speaker, and other suitable components. In an embodiment, the audio components 207 are connected to the bus 208. Alternatively, the audio components 207 are themselves I/O devices, and are connected with the bus 208 using the I/O device interface 204, or in another suitable configuration.

The CPU 202 retrieves and executes programming instructions stored in the memory 210 as well as stores and retrieves application data residing in the storage 270. The bus 208 is used to transmit programming instructions and application data between the CPU 202, the I/O device interface 204, the storage 270, the network interface 206, and the memory 210. The CPU 202 is included to be representative of a CPU, multiple CPUs, a single CPU having multiple processing cores, graphics processing units (GPUs) having multiple execution paths, and the like. The memory 210 is generally included to be representative of electronic storage of any suitable type(s), including random access memory or non-volatile storage. The storage 270 may be a disk drive storage device. Although shown as a single unit, the storage 270 may be a combination of fixed and/or removable storage devices, such as fixed disc drives, removable memory cards, network attached storage (NAS), or a storage area-network (SAN).

Illustratively, the memory 210 includes an operating system 240, while the storage 270 includes a data repository (e.g., a database). The operating system 240 generally controls the execution of application programs on the user device 200. Examples of operating system 240 include, without limitation, mobile operating systems, versions of UNIX, distributions of the Linux® operating system, versions of Microsoft® Windows® and so on.

The memory 210 generally includes program code for performing various functions related to monitoring biometric data. The program code is generally described as various functional "applications," "components," or "modules" within the memory 210, although alternate implementations may have different functions and/or combinations of functions. Within the memory 210, the patient care application 220 is generally configured to interface with and control the biometric monitoring devices (e.g., the sensor devices 141, 142, and 143 illustrated in FIG. 1).

The patient care application 220 further includes a voice control module 222. The voice control module 222 is generally configured to facilitate a user providing voice commands to the user device 200. This is discussed in more detail in relation to FIGS. 3-5. The patient care application 220 further includes an audio guidance module 224. The audio guidance module 224 is generally configured to facilitate providing audio guidance to a user through the user device 200. This is discussed in more detail in relation to FIGS. 3-5.

The memory 210 further includes a care plan 225. As discussed above in relation to FIG. 1, a care plan 225 may be created based on one or more care protocols, with each of the care protocols relating to a respective medical condition the patient has been diagnosed with. A care protocol is a set of tasks that a patient follows to manage a certain condition, metrics that can be monitored, objectives for the patient to meet, and the like. In an embodiment, the care plan 225 is stored in the storage 270 and accessed using the memory 210 during operation of the user device 200.

Figure 3:
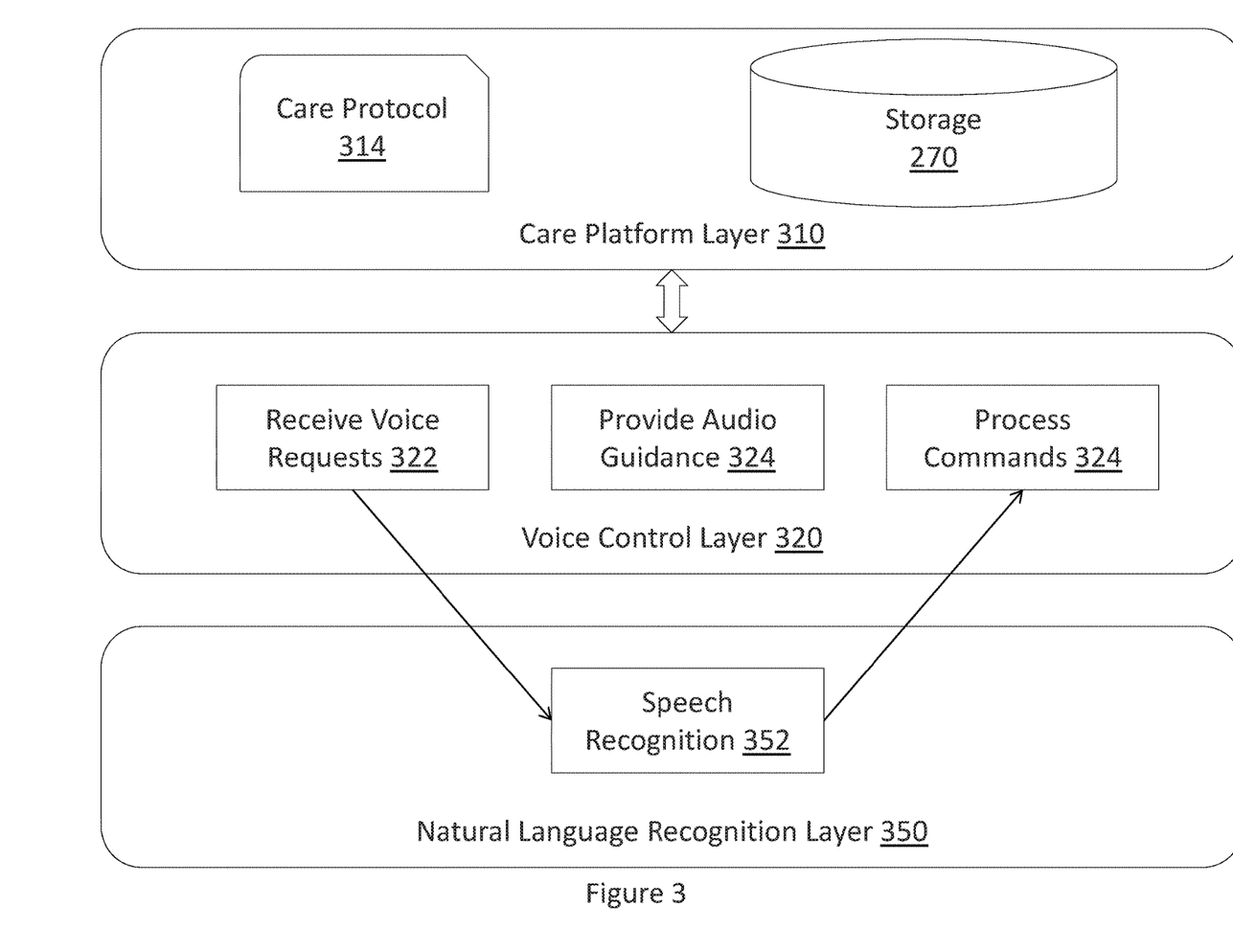
FIG. 3 is a block diagram illustrating voice control and guidance in a patient care environment, according to one embodiment.

FIG. 3 is a block diagram illustrating voice control and guidance in a patient care environment, according to one embodiment described herein. In an embodiment, the environment can be described using three layers. A care platform layer 310 includes a care protocol 314 and a storage 270. In an embodiment, the care protocol 314 is a component of the care plan 225 described above in relation to FIGS. 1 and 2. For example, the care protocol 314 can specify tasks, symptoms, devices, monitoring modes, start and end dates, and the like, to manage a certain condition. In an embodiment, the care platform layer can include multiple care protocols 314, relating to multiple conditions. In an embodiment, the storage 270 includes data for use by a voice control module (e.g., the voice control module 222 illustrated in FIG. 2) and an audio guidance module (e.g., the audio guidance module 224 illustrated in FIG. 2). For example, the storage 270 can include .wav files or other audio files for use by the audio guidance module 224. As another example, the storage 270 can include a vocabulary relating to user requests for use by the voice control module 222.

A voice control layer 320 includes features related to voice control and guidance in a patient care environment. In an embodiment, the voice control layer 320 can receive voice requests 322, provide audio guidance 324, and process commands 324. A natural language recognition layer 350 includes speech recognition service 352. In an embodiment, the speech recognition service 352 is configured to provide natural language recognition (e.g., using a third party SDK or a proprietary service). The features of the voice control layer 320 and the natural language recognition layer 350 are discussed further in relation to FIGS. 4 and 5.

In an embodiment, the voice control layer can receive voice requests 322 and provide the requests to the speech recognition service 352. For example, the voice control module 222 can record voice requests and transmit the recorded audio to the speech recognition service 352. As another example, the voice control module 222 can provide streaming audio to the speech recognition service 352. In an embodiment, the speech recognition service 352 analyzes the audio and generates a textual representation of the voice request. In an embodiment, the speech recognition service 352 provides the response to the voice control layer using a suitable network service API (e.g., JavaScript Object Notation (JSON)). The voice control module 222 can receive the textual representation, identify the command, and carry out the command.

Figure 4:
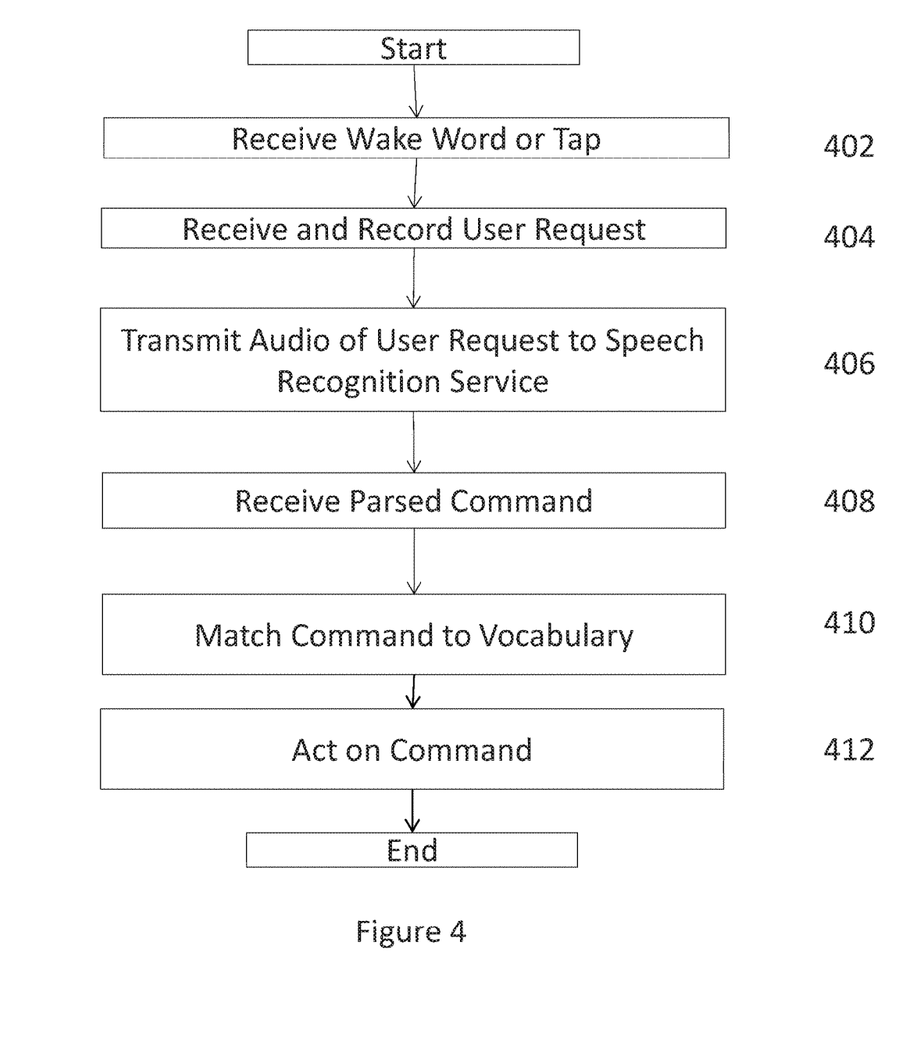
FIG. 4 is a flow chart illustrating voice control in a patient care environment, according to one embodiment.

FIG. 4 is a flow chart illustrating voice control in a patient care environment, according to one embodiment described herein. At block 402, the voice control module 222 receives a wake word or tap, from a user. For example, the voice control module 222 can be configured to wake the voice control functionality upon hearing a specific word from the user. Alternatively, the voice control module 222 can be configured to wake upon receiving a tap, or a specific button press (e.g., from the I/O device interface 204 of the user device 200). In an embodiment, the voice control module 222 is now ready to receive a voice command.

At block 404, the voice control module 222 receives and records a voice request from a user. In an embodiment, the voice control module 222 receives a voice command using an audio component (e.g., a microphone in the audio components 207 illustrated in FIG. 2), records the voice command, stores the voice command on the user device 200 (e.g., in the memory 210 or the storage 270). At block 406, the voice control module 222 transmits the audio of the user request to the speech recognition service (e.g., the speech recognition service 352) using a communication network (e.g., the Internet or another suitable network). In an embodiment, the voice control module 222 records audio of the voice command and transmits the recorded audio to the speech recognition service 352. Alternatively, the voice control module 222 transmits streaming audio of the voice command to the speech recognition service 352. In an embodiment, the voice control module 222 transmits compressed audio to the speech recognition service 352.

At block 408, the voice control module 222 receives from the speech recognition service 352 a parsed command. In an embodiment, the voice control module 222 receives a textual representation of the user's voice command. Alternatively, the voice control module 222 can receive another suitable representation of the voice command (e.g., a data structure defined by the speech recognition service to represent the voice command, a code representing the voice command, or any other suitable representation).

At block 410, the voice control module 222 matches the parsed command to a vocabulary. In an embodiment, the storage 270 includes a vocabulary relating to available commands. At block 410, the voice control module 222 matches the parsed command to this vocabulary to determine the requested command. In an embodiment, the care protocol (e.g., the care protocol 314) includes a portion (or all) of the vocabulary used to determine the requested command. For example, the care protocol 314 can include terms used by the voice control module 222 to determine the requested command.

Alternatively, or in addition, in an embodiment, the care protocol 314 can provide context to assist in matching the parsed command with the vocabulary. For example, the care protocol 314 can provide treatment options and likely symptoms. The voice control module 222 can use this information to supplement or modify the vocabulary. Alternatively, the voice control module 222 can use the information in the care protocol to provide context for matching with the vocabulary. For example, information in the care protocol 314 can be used to assist in matching the parsed command with a vocabulary (e.g., a parsed command that appears close to a symptom or treatment option described in the care protocol 314 can be matched with that symptom or treatment option).

In this way, the care protocol 314 can be used to assist in the speech recognition. In an embodiment, using the care protocol 314 to provide the vocabulary or assist in matching the command further allows for dynamic extension of the patient care application (e.g., the patient care application 220). For example, the available voice commands for the voice control module 222 can be extended or modified based on the care protocol 314, without modifying the voice control module 222 itself.

At block 412, the voice control module 222 acts on the matched command. For example, if the command requests information, the voice control module 222 can instruct the user device to play audio with the desired information. As another example, if the command provides symptom or biometric information, the voice control module 222 can provide this information to the patient care application 220 for storage and use.

Figure 5:
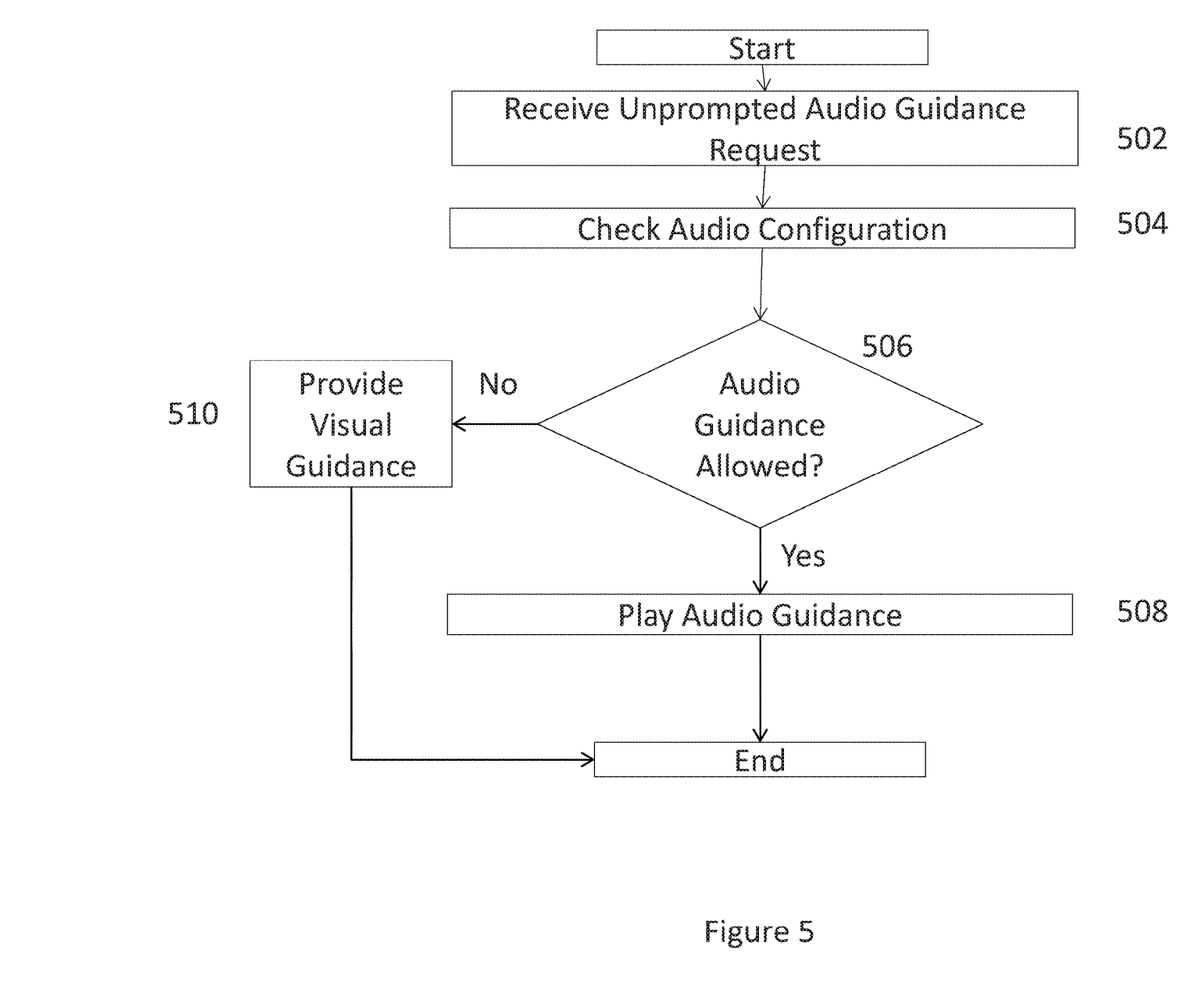
FIG. 5 is a flow chart illustrating voice guidance in a patient care environment, according to one embodiment.

FIG. 5 is a flow chart illustrating voice guidance in a patient care environment, according to one embodiment described herein. At block 502, the audio guidance module 224 receives an unprompted audio guidance request. For example, the patient care application 220 can trigger an alert or reminder and can provide a request to the audio guidance module 224 to provide audio guidance relating to this alert or reminder. In an embodiment, the patient care application 220 can determine audio guidance based on the importance of the underlying message. For example, informational messages can be provided visually, or to the audio guidance module 224 only if a user specifically requests audio or enables an audio preference. But urgent messages can be provided both visually and by audio, to help ensure that the patient receives the message. In an embodiment, urgent or otherwise important messages can be provided by audio whether or not the user has configured audio guidance.

At block 506, the audio guidance module 224 determines whether audio guidance is allowed. In an embodiment, the user can configure whether to allow audio guidance. This allows the user to keep the patient care application 220 discrete, if he or she does not wish it to play audio. In an embodiment, the audio guidance module 224 can also provide audio guidance in response to a prompted request from a user (e.g., a voice command, or a tap requesting audio guidance). In this circumstance, the audio guidance module 224 can proceed to block 508 and provide the requested audio guidance.

If audio guidance is not allowed, at block 510 the patient care application provides visual guidance (e.g., textual or graphical guidance). If audio guidance is allowed, at block 508 the audio guidance module 224 plays the audio guidance. For example, the storage 270 can include pre-recorded audio files representing audio guidance. The audio guidance module 224 can select and play a suitable audio file. Alternatively, the audio guidance module 224 can include a text recognition module capable of recognizing text and automatically generating corresponding audio. The storage 270 can include a textual description of the guidance, and the audio guidance module 222 can generate (and play) audio corresponding to the text description.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system."

Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

We claim:

1. A computer-implemented method for voice control of a patient care device, comprising:

receiving an audio request from a user at the patient care device;

recording the audio request using the patient care device;

transmitting, using a computer processor, the audio request over a communication network from the patient care device to a speech recognition service, and in response receiving, from the speech recognition service, a parsed representation of the audio request;

matching the parsed representation, using the computer processor, to a first command in a vocabulary of available commands, and in response performing the first command at the patient care device;

receiving a request from a user, at the patient care device, for audio guidance; and determining, at the patient care device, that audio guidance is not allowed and, in response, providing visual guidance to the user in place of audio guidance, wherein the vocabulary relates to a care protocol for treating a patient, wherein matching the parsed representation to the first command in the vocabulary of available commands comprises matching the parsed representation with at least a portion of the care protocol, and wherein the first command relates to at least one of a symptom included in the care protocol or a treatment included in the care protocol.

2. The computer-implemented method of claim 1, wherein the first command is identified in the vocabulary of available commands based on a treatment described in the care protocol.

3. The computer-implemented method of claim 1, wherein the first command is identified in the vocabulary of available commands based on a symptom described in the care protocol.

4. The computer-implemented method of claim 1, further comprising:

receiving, at the patient care device, the care protocol for treating the patient; and modifying the vocabulary based on the received care protocol.

5. The computer-implemented method of claim 1, further comprising:

transmitting, using the computer processor, a second audio request over the communication network from the patient care device to the speech recognition service, and in response receiving, from the speech recognition service, a second parsed representation of the second audio request;

matching the parsed representation, using the computer processor, to a second command in the vocabulary of available commands, comprising:

determining the second command in the vocabulary of available commands using the care protocol, wherein the second parsed representation does not appear in the care protocol; and performing the second command at the patient care device.

6. The computer-implemented method of claim 1, wherein the parsed representation comprises one of: a textual representation of the audio request, a data structure representation of the audio request, or a code representation of the audio request.

7. The computer computer-implemented method of claim 1, further comprising:

identifying, using the computer processor, an audio configuration parameter for the patient care device; and determining, based on the audio configuration parameter and using the computer processor, that voice commands are allowed, wherein the transmitting the audio request to the speech recognition service occurs based on the determining that voice commands are allowed.

8. A computer program product for voice control of a patient care device, the computer program product comprising:

a non-transitory computer-readable storage medium that is tangible and having computer-readable program code embodied therewith, the computer-readable program code executable by one or more computer processors to perform an operation, the operation comprising:

receiving an audio request from a user at the patient care device;

recording the audio request using the patient care device;

transmitting the audio request over a communication network from the patient care device to a speech recognition service, and in response receiving, from the speech recognition service, a parsed representation of the audio request;

matching the parsed representation to a first command in a vocabulary of available commands, and in response performing the first command at the patient care device;

receiving a request from the user, at the patient care device, for audio guidance; and determining, at the patient care device, that audio guidance is not allowed and, in response, providing visual guidance to the user in place of audio guidance, wherein the vocabulary relates to a care protocol for treating a patient, wherein matching the parsed representation to the first command in the vocabulary of available commands comprises matching the parsed representation with at least a portion of the care protocol, and wherein the first command relates to at least one of a symptom included in the care protocol or a treatment included in the care protocol.

9. The computer program product of claim 8, wherein the first command is identified in the vocabulary of available commands based on a treatment described in the care protocol.

10. The computer program product of claim 8, the operation further comprising:

receiving, at the patient care device, the care protocol for treating the patient; and modifying the vocabulary based on the received care protocol.

11. The computer program product of claim 8, the operation further comprising:

transmitting a second audio request over the communication network from the patient care device to the speech recognition service, and in response receiving, from the speech recognition service, a second parsed representation of the second audio request;

matching the parsed representation to a second command in the vocabulary of available commands, comprising:

determining the second command in the vocabulary of available commands using the care protocol, wherein the second parsed representation does not appear in the care protocol; and performing the second command at the patient care device.

12. The computer program product of claim 8, the operation further comprising:

identifying, using the computer processor, an audio configuration parameter for the patient care device;

determining, based on the audio configuration parameter and using the computer processor, that voice commands are allowed, wherein the transmitting the audio request to the speech recognition service occurs based on the determining that voice commands are allowed; and receiving a command at the patient care device to enable voice commands, and in response modifying the audio configuration parameter.

13. A system, comprising:

a processor; and a memory storing a program, which, when executed on the processor, performs an operation for voice control of a patient care device, the operation comprising:

receiving an audio request from a user at the patient care device;

recording the audio request using the patient care device;

transmitting the audio request over a communication network from the patient care device to a speech recognition service, and in response receiving, from the speech recognition service, a parsed representation of the audio request;

matching the parsed representation to a first command in a vocabulary of available commands, and in response performing the first command at the patient care device;

receiving a request from the user, at the patient care device, for audio guidance; and determining, at the patient care device, that audio guidance is not allowed and, in response, providing visual guidance to the user in place of audio guidance, wherein the vocabulary relates to a care protocol for treating a patient, wherein matching the parsed representation to the first command in the vocabulary of available commands comprises matching the parsed representation with at least a portion of the care protocol, and wherein the first command relates to at least one of a symptom included in the care protocol or a treatment included in the care protocol.

14. The system of claim 13, wherein the first command is identified in the vocabulary of available commands based on a treatment described in the care protocol.

15. The system of claim 13, the operation further comprising:
  receiving, at the patient care device, the care protocol for treating the patient; and
  modifying the vocabulary based on the received care protocol.

16. The system of claim 13, the operation further comprising:
  transmitting a second audio request over the communication network from the patient care device to the speech recognition service, and in response receiving, from the speech recognition service, a second parsed representation of the second audio request;
  matching the parsed representation to a second command in the vocabulary of available commands, comprising:
    determining the second command in the vocabulary of available commands using the care protocol, wherein the second parsed representation does not appear in the care protocol; and
  performing the second command at the patient care device.

* * * * *